(12) United States Patent
Suzuki et al.

(10) Patent No.: US 6,706,029 B1
(45) Date of Patent: *Mar. 16, 2004

(54) DISPOSABLE DIAPER

(75) Inventors: Migaku Suzuki, Kanagawa-ken (JP); Mitsuzo Ochi, Ehime-ken (JP); Takeshi Kudo, Ehime-ken (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/649,091

(22) Filed: Aug. 28, 2000

Related U.S. Application Data

(63) Continuation-in-part of application No. 08/908,002, filed on Aug. 11, 1997, now abandoned, which is a continuation of application No. 08/792,728, filed on Jan. 31, 1997, now abandoned, which is a continuation of application No. 07/378,234, filed as application No. PCT/JP88/00888 on Sep. 5, 1988, now abandoned.

(30) Foreign Application Priority Data

Sep. 7, 1987 (JP) .......................................... 62-223780

(51) Int. Cl.⁷ .......................... A61F 13/15; A61F 13/20
(52) U.S. Cl. .............................. 604/385.28; 604/385.01
(58) Field of Search ................................. 604/374–377, 604/385.01, 386, 389–391, 393–397, 401–402, 385.19, 385.24–385.3

(56) References Cited

U.S. PATENT DOCUMENTS

| | | | | |
|---|---|---|---|---|
| 2,545,674 A | * | 3/1951 | Ralph | 604/394 |
| 2,652,057 A | * | 9/1953 | Siegel et al. | 604/394 |
| 2,893,393 A | * | 7/1959 | Pressley | 604/394 |
| 3,572,342 A | * | 3/1971 | Lindquist | 604/369 |
| 4,500,316 A | | 2/1985 | Damico | |
| 4,597,761 A | | 7/1986 | Buell | |
| 4,617,022 A | * | 10/1986 | Pigneul et al. | 604/391 |
| 4,657,539 A | | 4/1987 | Hasse | |
| 4,704,115 A | | 11/1987 | Buell | |
| 4,704,117 A | | 11/1987 | Mitchell | |
| 4,743,246 A | | 5/1988 | Lawson | |
| 4,808,178 A | * | 2/1989 | Aziz et al. | 604/385.28 |
| 4,822,435 A | | 4/1989 | Igaue et al. | |
| 4,834,740 A | | 5/1989 | Suzuki et al. | |
| 4,834,741 A | | 5/1989 | Sabee | |
| RE33,106 E | | 11/1989 | Beckestrom | |
| 4,900,384 A | | 2/1990 | Sanders et al. | |
| 4,904,251 A | | 2/1990 | Igaue et al. | |
| 5,429,632 A | * | 7/1995 | Tanji et al. | 604/395 |
| 5,439,459 A | * | 8/1995 | Tanji et al. | 604/385.28 |

FOREIGN PATENT DOCUMENTS

| | | | |
|---|---|---|---|
| EP | 0219326 | 4/1987 | |
| EP | 0243013 | 10/1987 | |
| EP | 0251332 | 1/1988 | |
| JP | 41-18359 | 8/1966 | |
| JP | 58-65002 | 4/1983 | |
| JP | 58-87301 | 5/1983 | |
| JP | 61-296103 | 12/1986 | |
| JP | 62-88704 | 6/1987 | |
| JP | 6-197925 | * 7/1994 | 604/396 |

* cited by examiner

Primary Examiner—Karin Reichle
(74) Attorney, Agent, or Firm—Lowe Hauptman Gilman & Berner LLP

(57) ABSTRACT

A diaper structure is formed with a leakage preventing arrangement, in the form of a flexible flap located outwardly with respect to a diaper absorbent core. The flap is formed with a support portion extending upwardly from the diaper surface to support an inwardly extending inner branched portion and an outwardly extending outer branched portion extending the length of the support portion. Both the inner and outer branched portions are fixed to the diaper body at longitudinal ends thereof in longitudinally stretched condition so that a pocket is jointly formed by a portion of a topsheet covering a side edge of the core, the support portion and the inner branched portion. The pocket is maintained in an open position independently of a wearer's posture to impede the leakage of excretions from the diaper.

13 Claims, 3 Drawing Sheets

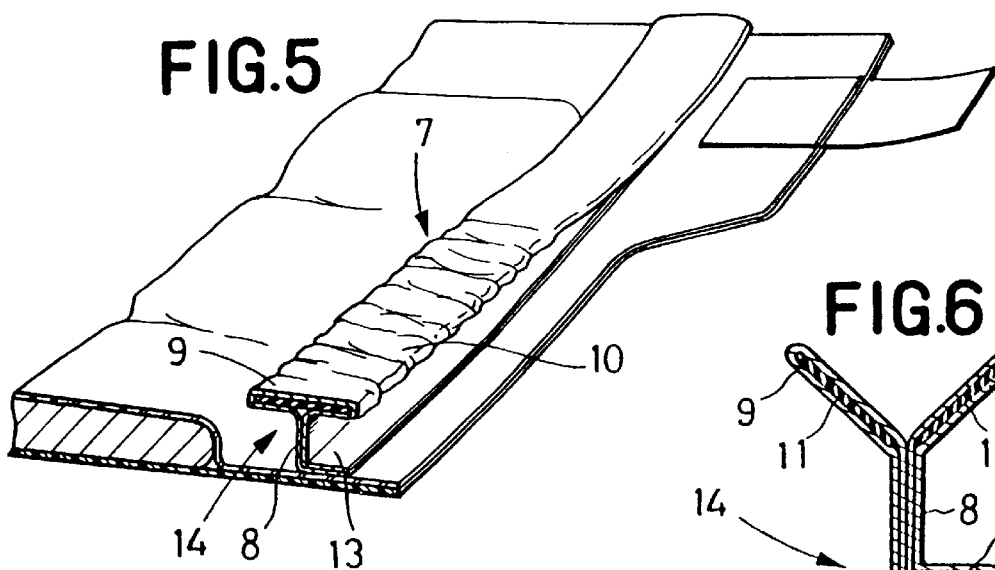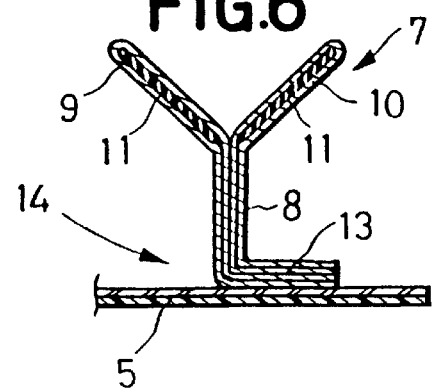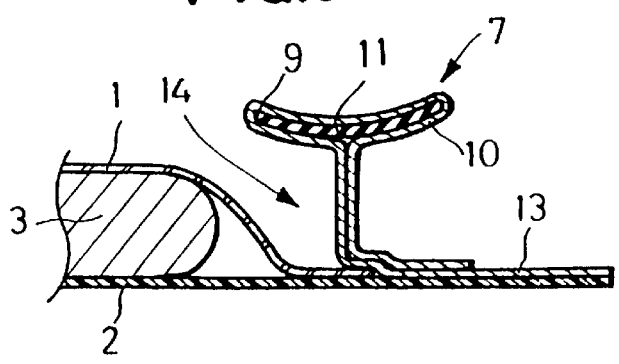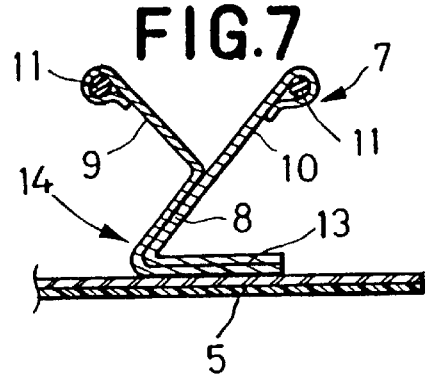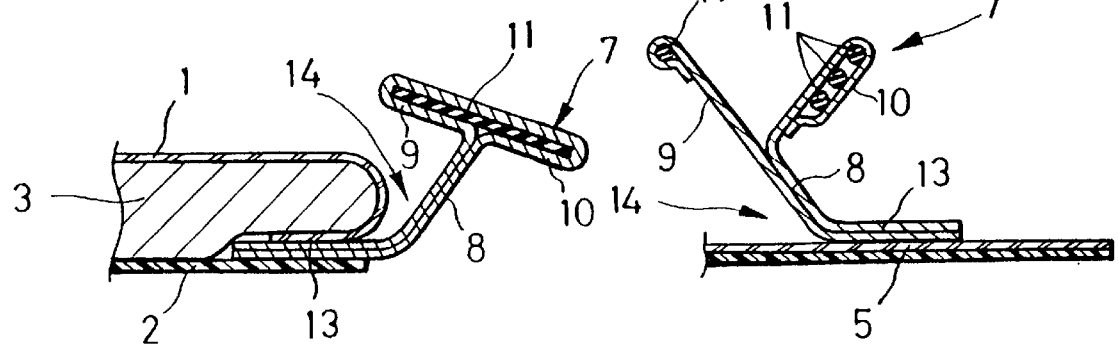

DISPOSABLE DIAPER

RELATED APPLICATIONS

The present application is a continuation-in-part of prior application Ser. No. 08/908,002, filed Aug. 11, 1997, now abandoned, which is a continuation of prior application Ser. No. 08/792,728, filed on Jan. 31, 1997, now abandoned, which is a continuation of application Ser. No. 07/378,234 filed on Feb. 4, 1992, now abandoned, which was the National Stage of International Application No. PCT/JP88/00888 filed on Sep. 5, 1988.

TECHNICAL FIELD

The present invention relates to a disposable diaper of a type requiring no diaper cover and more particularly to such diaper provided in areas surrounding respective thighs and/or waist with leakage preventing means containing elastic flaps.

BACKGROUND TECHNIQUE

The U.K. Patent Disclosure Gazette No. 2,181,336A discloses garments such as disposable diapers, which are provided with leakage preventing means comprising elastic flaps for fitting around the respective thighs of the wearer. The leakage preventing means disclosed therein comprises first flaps extending outwardly and provided with respective elastic members, and second flaps each having one side edge provided with an elastic member and the opposite side edge connected to a main body of the article wherein said one side edge is collapsed inwardly and, in this condition, subjected to fixation at longitudinally opposite ends thereof.

Each of said second flaps is provided to form a pocket adapted to block transverse flow of any excretions as this second flap is allowed to be raised under the contractile force of the elastic member associated therewith. With an article having such construction, said pockets are opened around the thighs of the wearer with said second flaps being raised under the contractile force of the respective elastic members against the crotch area (an area defined between both thighs) Simultaneously, said first flaps have been folded on the inner sides of the article and pressed against the respective thighs under the effect of the associated elastic members. In such a situation, the folding lines of said first flaps are in coincidence with base lines of the corresponding second flaps, i.e., the lines along which said second flaps are connected to the main body of the article, and said second flaps are not pressed against the thighs.

It should be noted here that the degree to which each of said pockets is opened depends upon the angle at which the corresponding second flap is raised. For example, when the wearer takes a posture with the thighs largely outstretched so as to stretch said second flaps, or when the wearer sits down with said second flaps inwardly collapsed, said pockets are insufficiently opened so that the desired blocking effect of said pockets against excretions, particularly such as loose feces and urine, can not be obtained and this inconveniently results in leakage thereof.

A primary object of the present invention is to resolve the problem as above mentioned and to provide a leakage preventing means for disposable diapers that is adapted to achieve a sealing effect sufficiently high to block leakage of excretions.

DISCLOSURE OF THE INVENTION

The present invention is directed to disposable diaper comprising a liquid-permeable topsheet, a liquid-impermeable backsheet, an absorbent core sandwiched between both sheets, and a leakage preventing means subjected to the effect of elastic members.

Said leakage preventing means comprises flexible flaps and elastic members, said flaps each including a support portion extending upwardly from the main body of the diaper, an inner branched portion extending inwardly from said support portion, an outer branched portion extending outwardly from said support portion and said elastic member being disposed in association with both said inner and outer branched portions so as to form elastic gathers in these portions.

It is most preferable to dispose a pair of such leakage preventing means, for use around the legs of the wearer, along opposite sides of said absorbent core longitudinally thereof so that the inner branched portions are usually pressed under the effect of the elastic members against the respective thighs rather than the crotch area, and the pockets formed at least by respective inner surfaces of said inner branched portions and the associated support portions are maintained in their adequately opened positions independently of the posture taken by the wearer. As a consequence, said pockets can effectively block leakage of excretions, particularly of loose faces and urine. Simultaneously, said inner branched portions cooperate with said outer branched portions to achieve the high sealing effect necessary to block leakage of excretions, since said outer branched portions located adjacent said inner branched portions are also elastically pressed against the respective thighs.

Said leakage preventing means may also be disposed along the waist line of diaper, if desired, to achieve the same good sealing effect.

Stated differently, the present invention concerns a disposable diaper having a front, a back and lateral sides and further including a liquid permeable topsheet, a liquid impermeable backsheet, and absorbent core sandwiched between these sheets, and excrement leakage preventing means in the form of flexible flaps located outwardly with respect to the absorbent core. Each flexible flap comprises a support portion extending upwardly with respect to the surface of the diaper. An inner branched portion, an entire length of which extends inwardly from an upper part of the support portion, is generally parallel to the backsheet. An outer branch portion, the entire length of which extends outwardly from the upper part of the support portion, is also generally parallel to the backsheet. At least one elastic member is incorporated into both the inner and outer branch portions to form elastic gathers in these two portions. A pocket is formed by an inner surface of a support portion and the inner branch portion which serves to impede the leakage of excretions from the diaper.

The diaper inner branched portion includes an upper segment which extends inwardly from an upper part of the support portion parallel to the backsheet and a lower segment extending outwardly towards the support portion generally parallel to the backsheet.

In another aspect, the outer branched portion includes an upper segment extending outwardly from an upper part of tie support portion generally parallel to the backsheet and a lower segment extendingly inwardly toward the support portion generally parallel to the backsheet.

Preferably, at least one elastic member extends parallel to the backsheet.

Preferably, the inner branched portion has a width greater than a thickness thereof. Likewise, the outer branch portion preferably has a width greater than the thickness thereof.

In accordance with the further feature, the support portion, the inner branch and the outer branch portion are together formed from the same strip of material that is doubled onto itself to form the portions. The at least one elastic member extends a full width of both the inner and outer branch portions.

The width of at least one of the inner and outer branch portions is approximately equal to a height of the support portion in a preferred embodiment.

The invention also concerns a disposable diaper having a front, a back and lateral sides and further includes a liquid permeable topsheet, a liquid impermeable backsheet, and an absorbent core sandwiched between the sheets and excrement leakage preventing means in the form of flexible flaps located outwardly with respect to the absorbent core. The flexible flap comprising a support portion extending upwardly with respect to the surface of the diaper. An inner branch portion, having a width which extends about one half a distance between the support portion and an outer most longitudinal edge of the core and extending from an upper part of the support portion, is generally parallel to the backsheet. An outer branch portion extends outwardly from the support portion generally parallel to the backsheet. At least one elastic member is incorporated into both of the inner and outer branch portions to form elastic gathers in these two portions. A pocket is formed by an inner surface of the support portion and the inner branch portion which serves to impede the leakage of excretions from the diaper.

In a preferred embodiment of this invention, each inner branch and outer branch portion is elongate and has a top surface which is flat. Each branch portion can be bent upwardly and downwardly from the upper end of the support from which they project so that each branch is independently deformable to closely contact a wearer's skin. For this purpose, the length and flexibility of each branch, particularly the inner branch portion, must be adequate in the direction from which it extends from the support portion. In the preferred embodiment, each branch has a length in the direction of the absorbent core which is at least three times as large as the thickness of the associated support.

In the preferred embodiment, the opposite longitudinal ends of each of the inner and outer branch portions are preferably fixed to the topsheet which advantageously assures that the pocket is opened and stabilized in the position depicted in FIG. 2. In a variation of the preferred embodiment, it is preferred that at least the opposite ends of the inner branch portion be fixed in their longitudinally stretched condition to ensure close contact with a wearer's skin by virtue of the elongation stress of the elastic member contained in the branch.

In the preferred embodiment, the flexible flap is formed with a T-shape in cross-section as defined by the support portion and the inner and outer branch portions which ensures a more stable contact with a wearer's skin as compared with a flap, for example, in the form of an L-shape.

The support portion, the inner branch portion and the outer branch portion are together formed from the same strip of material that is doubled onto itself to form the portions. At least one elastic member extends the full width of both inner and outer branch portions. Preferably, a width of at least one of the inner and outer branch portions is approximately equal to a height of the support portion. Also preferably, the inner branch portion includes a width greater than a thickness and the outer branch portion also includes a width greater than a thickness.

In accordance with another aspect of the invention, a disposable diaper has a back and lateral sides and further includes a liquid permeable topsheet, a liquid impermeable backsheet and absorptive core sandwiched between the sheets, and excrement leakage preventing means in the form of at least one flexible flap located outwardly with respect to the absorbent core. The at least one flexible flap comprises a support portion extending upwardly with respect to a surface of the diaper. This support portion supports a outer branch portion which extends outwardly from an upper part of the support portion and an inner branch portion which extends inwardly from the upper part of the support portion. At least one elastic member is incorporated into both the inner and outer branch portions to form elastic gathers into these two portions. Both the inner and outer branch, portions are fixed to a body of the diaper at longitudinal ends thereof and under longitudinally stretched conditions of the elastic member so that the inner branch portions and at least a top part of the supporting portion extend upwardly of a top surface of a top sheet and above an area defined by a top surface of the core with the inner branch portion spaced away from the top surface of the topsheet under the elastically contractible force of the elastic member. A pocket is jointly formed by the top sheet covering a side edge of the core, the support portion and the inner branch portion. The pocket is thereby maintained in an open position independently of a wearer's posture to impede the leakage of excretions from the diaper.

BRIEF DESCRIPTION OF THE DRAWINGS

FIG. 5 is a fragmentary perspective view corresponding to FIG. 2;

FIGS. 6 through 10 are sectional views showing further variants of said leakage preventing means;

MOST PREFERRED EMBODIMENTS OF THE INVENTION

The present invention will be described in reference with the accompanying drawings.

Figure 1:
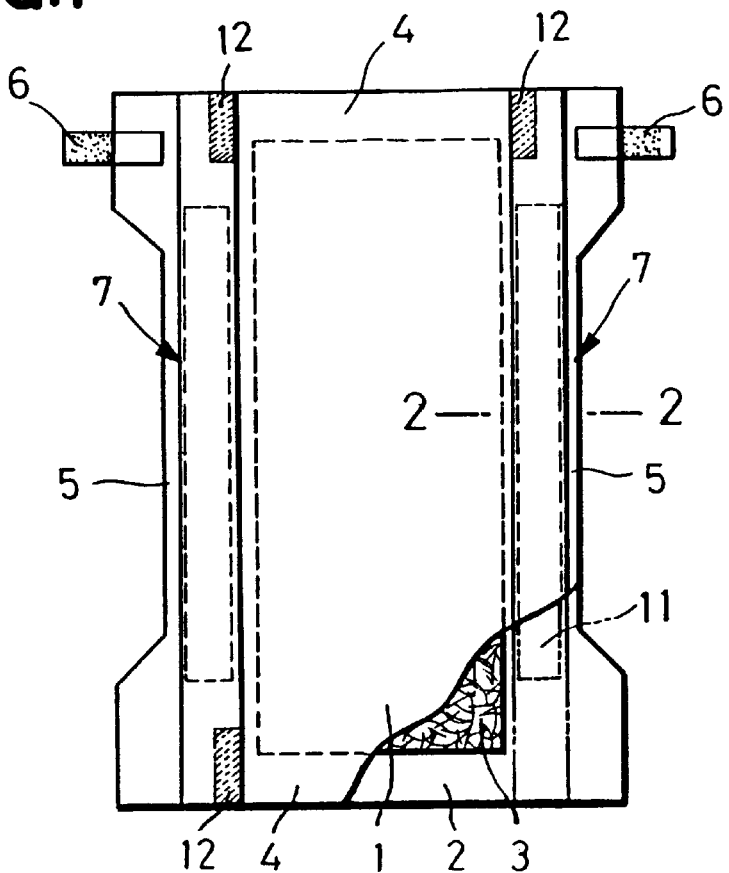
FIG. 1 is a developed plan view, partially broken away, of a diaper as one embodiment of the present invention.

Referring to FIG. 1, the diaper comprises a liquid-permeable topsheet 1, a liquid-impermeable backsheet 2, an absorbent core 3 sandwiched between these both sheets, waist and side flaps 4, 5 formed by portions of said both sheets outwardly extending from longitudinally opposite edges and from transversely opposite edges, respectively, of said absorbent core, and tape fasteners 6 attached to the rear waist flap at transversely opposite sides thereof.

Figure 2:
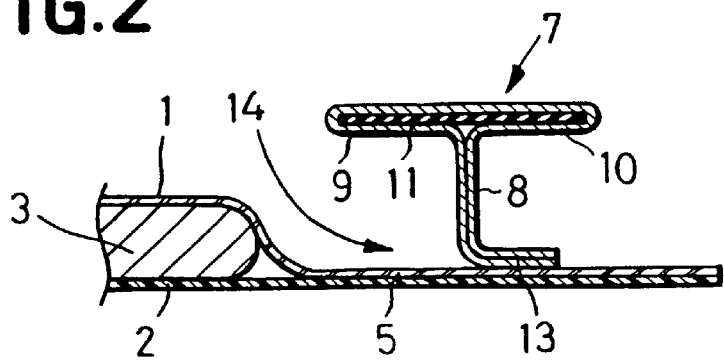
FIG. 2 is a sectional view taken along a line 2—2 in FIG. 1 preponderantly showing leakage preventing means constructed in accordance with the present invention.

As shown by FIG. 2, the diaper further comprises second flaps 7 extending longitudinally of the respective flaps 5. Each of the flaps 7 is formed from a single sheet defining a sleeve having a T-shaped cross-section which is defined by a support portion 8 fixed to the top surface of the associated flap 5, an inner branched portion 9 extending inwardly from the top end of said support portion, and an outer branched portion 10 extending outwardly from the top end of said support portion. The inner and outer branched portions 9, 10 contain therein a relatively wide elastic member 11 common to the both branched portions. The elastic member 11 must be positioned at least in the crotch area of the diaper.

The inner branched portion 9 and/or the outer branched portion 10 are or is preferably fixed to the associated flap 5 at longitudinally opposite ends or the longitudinal one end in the front area of the diaper. Such fixation may be achieved in various manners, i.e., by fixing the inner branched portion 9 at longitudinally opposite ends designated by reference numeral 12 in FIG. 1, by fixing the outer branched portion 10 at longitudinally opposite ends, by fixing both the inner and outer branched portions 9, 10 at longitudinally opposite ends (see FIG. 5), by fixing the inner branched portion at the longitudinal one end positioned in the front area of the diaper, by fixing the outer branched portion at the longitudinal one end positioned in the front area of the diaper or by fixing both the inner and outer branched portions 9, 10 at the longitudinal one end positioned in the front area of the diaper.

Figure 3:
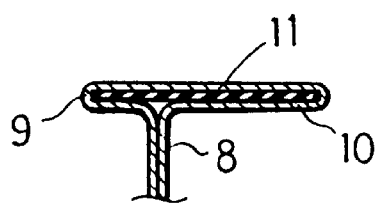
FIGS. 3 and 4 are sectional views, partially-broken away, showing variants of said leakage preventing means shown by FIG. 2, respectively.
Figure 4:
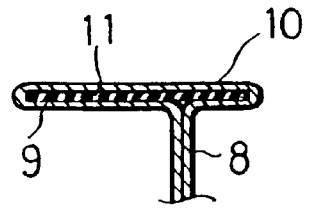

Concerning the widths by which the inner and outer branched portions 9, 10 laterally extend, respectively, the width of the inner branched portion may be substantially equal to that of the outer branched portion as seen in FIG. 2, the former may be less than the latter as seen in FIG. 3, or the former may be larger than the latter as seen in FIG. 4.

The manner in which the inner and outer branched portions are subjected to fixation at longitudinally opposite ends, as well as the widths by which these portions laterally extend, are selected so that the optimum condition of diaper wearing can be achieved in view of various factors such as a size of the diaper, a distance from the absorbent core 3 to each flap 7 and the height of the support portion 8.

Stated differently, the present invention concerns a disposable diaper having a front, a back and lateral sides and further including a liquid permeable topsheet, a liquid impermeable backsheet, and absorbent core sandwiched between these sheets, and excrement leakage preventing means in the form of flexible flaps located outwardly with respect to the absorbent core. Each flexible flap comprises a support portion extending upwardly with respect to the surface of the diaper. An inner branched portion, having an entire length which extends inwardly from the an upper part of the support portion, is generally parallel to the backsheet. An outer branch portion, the entire length of which extends outwardly from the upper part of the support portion, is also generally parallel to the backsheet. At least one elastic member is incorporated into both the inner and outer branch portions to form elastic gathers in these two portions. A pocket is formed by an inner surface of a support portion and the inner branch portion which serves to impede the leakage of excretions from the diaper.

The diaper inner branched portion includes an upper segment which extends inwardly from an upper part of the support portion parallel to the backsheet and a lower segment extending outwardly towards the support portion generally parallel to the backsheet.

In another aspect, the outer branched portion includes an upper segment extending outwardly from an tipper part of the support portion generally parallel to the backsheet and a lower segment extendingly inwardly toward the support portion generally parallel to the backsheet.

Preferably, at least one elastic member extends parallel to the backsheet.

Preferably, the inner branched portion has a width greater than a thickness thereof. Likewise, the outer branch portion preferably has a width greater than the thickness thereof.

In accordance with the further feature, the support portion, the inner branch and the outer branch portion are together formed from the same strip of material that is doubled onto itself to form the portions. The at least one elastic member extends a full width of both the inner and outer branch portions.

The width of at least one of the inner and outer branch portions is approximately equal to a height of the support portion in a preferred embodiment.

The invention also concerns a disposable diaper having a front, a back and lateral sides and further includes a liquid permeable topsheet, a liquid impermeable backsheet, and an absorbent core sandwiched between the sheets and excrement leakage preventing means in the form of flexible flaps located outwardly with respect to the absorbent core. The flexible flap comprises a support portion extending upwardly with respect to the surface of the diaper. An inner branch portion, having a width which extends about one half a distance between the support portion and an outer most longitudinal edge of the core and extending inwardly from an upper part of the support portion, is generally parallel to the backsheet. An outer branch portion extends outwardly from the support portion generally parallel to the backsheet. At least one elastic member is incorporated into both of the inner and outer branch portions to form elastic gathers in these two portions. A pocket is formed by an inner surface of the support portion and the inner branch portion which serves to impede the leakage of excretions from the diaper.

In a preferred embodiment of this invention, each inner branch and outer branch portion is elongate and has a top surface which is flat. Each branch portion can be bent upwardly and downwardly from the upper end of the support from which they project so that each branch is independently deformable to closely contact a wearer's skin. For this purpose, the length and flexibility of each branch, particularly the inner branch portion, must be adequate in the direction from which it extends from the support portion. In the preferred embodiment, each branch has a length in the direction of the absorbent core which is at least three times as large as the thickness of the associated support.

In the preferred embodiment, the opposite longitudinal ends of each of the inner and outer branch portions are preferably fixed to the topsheet which advantageously assures that the pocket is opened and stabilized in the position depicted in FIG. 2. In a variation of the preferred embodiment, it is preferred that at least the opposite ends of the inner branch portion be fixed in their longitudinally stretched condition to ensure close contact with a wearer's skin by virtue of the elongation stress of the elastic member contained in the branch.

In the preferred embodiment, the flexible flap is formed with a T-shape in cross-section as defined by the support portion and the inner and outer branch portions which ensures a more stable contact with a wearer's skin as compared with a flap, for example, in the form of an L-shape.

The support portion, the inner branch portion and the outer branch portion are together formed from the same strip of material that is doubled onto itself to form the portions. At least one elastic member extends the full width of both inner and outer branch portions. Preferably, a width of at least one of the inner and outer branch portions is approximately equal to a height of the support portion. Also preferably, the inner branch portion includes a width greater than a thickness and the outer branch portion also includes a width greater than a thickness.

In accordance with another aspect of the invention, a disposable diaper has a back and lateral sides and further includes a liquid permeable topsheet, a liquid impermeable backsheet and absorptive core sandwiched between the sheets, and excrement leakage preventing means in the form of at least one flexible flap located outwardly with respect to the absorbent core. The at least one flexible flap comprises a support portion extending upwardly with respect to a surface of the diaper. This support portion supports a outer branch portion which extends outwardly from an upper part of the support portion and an inner branch portion which extends inwardly from the upper part of the support portion. At least one elastic member is incorporated into both the inner and outer branch portions to form elastic gathers into these two portions. Both the inner and outer branch portions are fixed to a body of the diaper at longitudinal ends thereof and under longitudinally stretched conditions of the elastic member so that the inner branch portions and at least a top part of the supporting portion extend upwardly of a top surface of a top sheet and above an area defined by a top surface of the core with the inner branch portion spaced away from the top surface of the topsheet under the elastically contractible force of the elastic member. A pocket is jointly formed by the top sheet covering a side edge of the core, the support portion and the inner branch portion. The pocket is thereby maintained in an open position independently of a wearer's posture to impede the leakage of excretions from the diaper.

FIGS. 6 through 10 show the variants of the above-mentioned embodiment that have the same effect as that of said above-mentioned embodiment.

In the embodiment shown by FIG. 6, each of the flaps 7 comprises the inner and outer branched portions 9, 10 which are separately formed into corresponding sleeves containing therein the separate elastic members 11.

The flap 7 in the embodiment shown by FIG. 7 comprises the inner and outer branched portions 9, 10, the free side edges of which respectively wrap the corresponding string-like elastic members 11.

The flap 7 in the embodiment shown by FIG. 8 comprises the inner branched portion 9, the free side edge of which wraps a single string-like elastic member 11 and the outer branched portion 10 wrapping, substantially over its entire width, a plurality of the string-like elastic members 11.

The flap 7 in the embodiment shown by FIG. 9 comprises the inner and outer branched portions 9, 10 which are formed into a single T-shaped sleeve from a single sheet, said portions containing therein the elastic member 11 which is slightly upwards concave in cross-section. This embodiment is also characterized in that the width of the topsheet 1 is less than that of the backsheet 2 to provide the backsheet 2 with outer side areas free from the topsheet 1 and the base end of the support portion 8 is bonded to the backsheet 2 so as to cover said outer side area associated with this support portion 8.

In the embodiments shown by FIGS. 6 through 8, the flap 7 is formed from two separate sheets which are bonded to each other along substantially lower halves to form the support portion 8 and left separated from each other to be formed into the inner and outer branched portions 9, 10, respectively, resulting in a branching line generated along a border of the inner and outer branched portions 9, 10. As a consequence, the inner and outer branched portions 9, 10 tend to be bent upwardly in a V-shape along said branching line when the respective elastic members 11 are contracted to some extent. While the inner and outer branched portions 9, 10 in the embodiments shown be FIGS. 2 through 4 and 9 also are sometimes bent upwardly in U-shape, depending upon the extent to which the elastic member 11 is contracted, said V-shaped bend occurring in the embodiments shown by FIGS. 6 through 8 is more significant than in the embodiments shown by FIGS. 2 through 4 and 9. Also in the embodiments shown by FIGS. 6 through 9, the widths by which the inner and outer branched portions 9, 10 extend as well as the manner in which these portions are fixed at the longitudinal opposite ends or any one end may be appropriately selected as for the embodiments shown by FIGS. 2 through 4.

In the embodiments shown by FIGS. 2 through 9, the base end 13 of the support portion 8 preferably extends outwards relative to said support portion 8, but the present invention is not limited to this arrangement.

The flap 7 in the embodiment shown by FIG. 10 is identical in its shape and construction to that in the embodiment shown by FIG. 2 except that, in the former, the base end 13 of the support portion 8 is interposed and fixed between the portion of the topsheet 1 wrapping the side edge of the absorbent core 3 and the portion of the backsheet 2 underlying said portion of the topsheet 1.

In all the embodiments shown by FIGS. 2 through 10, the pocket 14 is formed by the inner surfaces of the support portion 8 and the inner branched portion 9, respectively. While the pocket 14 is formed even when the inner branched portion 9 and/or the outer branched portion 10 have or has been fixed at longitudinal opposite ends or one end, it is preferred to provide such fixation for assuring the direction in which the pocket is opened to be stabilized.

Figure 11:
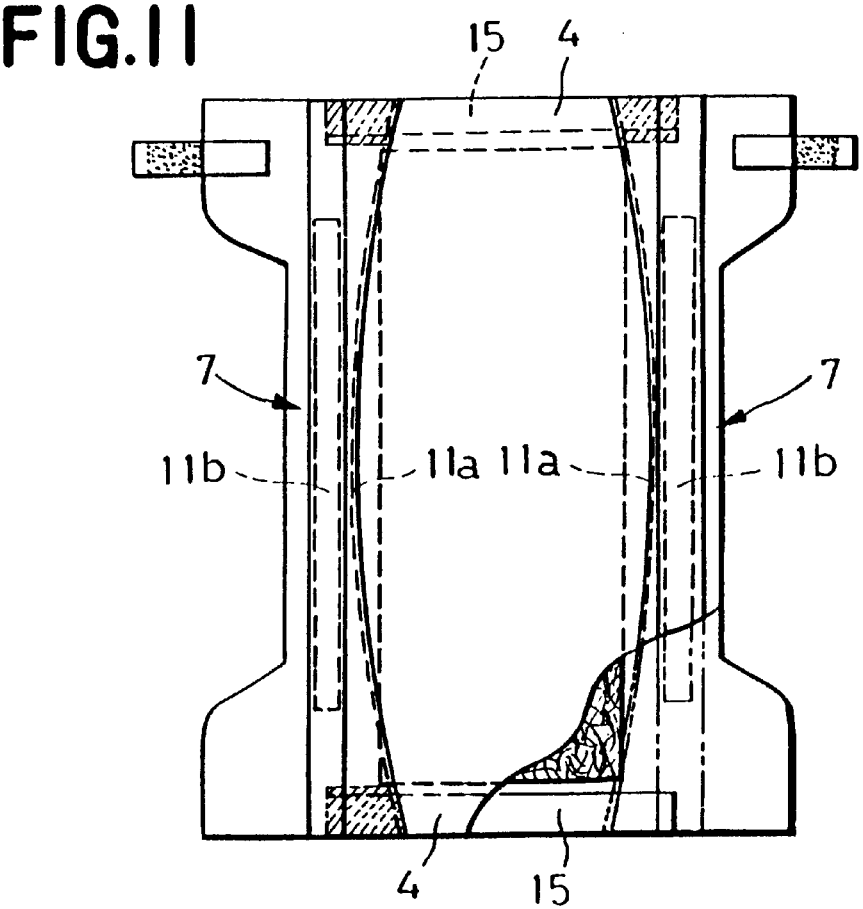
FIG. 11 is a developed plan view, partially broken away, of a diaper as another embodiment of the present invention.
Figure 12:
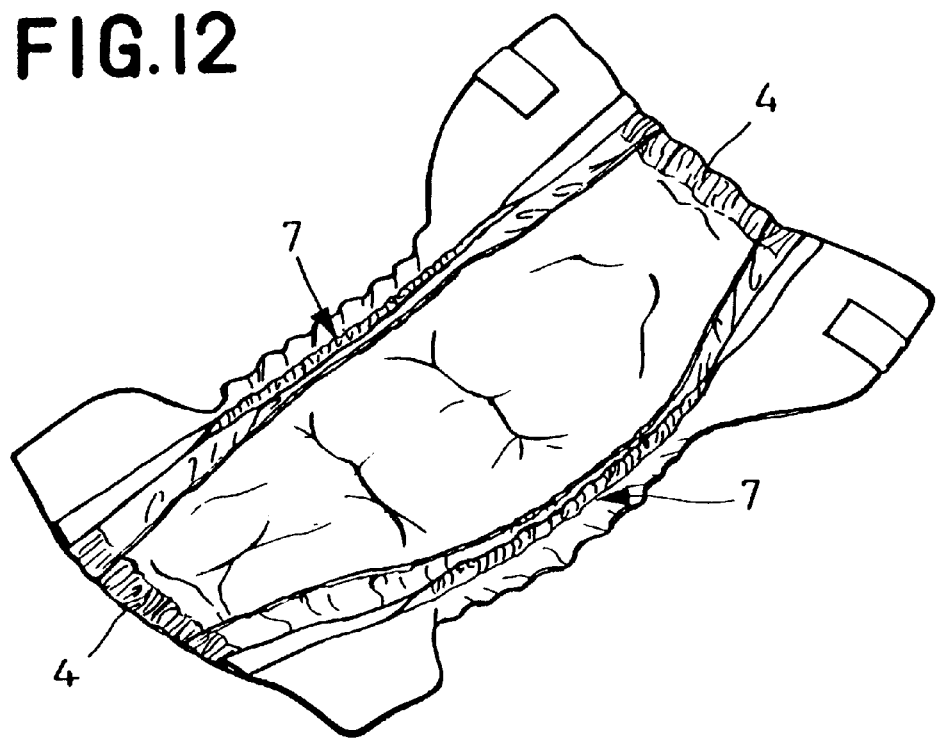
FIG. 12 is a perspective view corresponding to FIG. 11.

FIGS. 11 and 12 show a variant of the inner branched portion 9 in the previously mentioned embodiments. According to this variant, the pair of opposite inner branched portions 9 follow respective curves gradually coming nearer to each other from the middle area to the front and rear areas of the diaper and the string-like elastic members 11a are disposed along these respective curves. Along the outer branched portions 10, there are disposed relatively wide elastic members 11b. In this variant, there are provided relatively wide elastic members 15 between the topsheet 1 and the backsheet 2 along the respective waist flaps 4.

The topsheet 1 may be made of non-woven fabric, porous plastic film, or the like, the backsheet 2 may be made of air permeable plastic film, laminate sheet of said film and non-woven fabric, or the like, and the absorbent core 3 may be made of fluffy pulp, mixture of such pulp and highly absorptive polymer particles, or the like. Thus, the various kinds of material conventionally used for such diaper may be selectively used but the present invention is not limited to use of them.

The flap 7 is preferably made of material that is, at least partially, flexible as highly as possible, air-permeable, and water-impermeable. The flap 7 may be air-permeable and water-impermeable at the support portion 8, at the outer branched portion 10, at the support portion 8 and the outer branched portion 10, or at the support portion 8 and the inner branched portion 9 as well as the outer branched portion 10. Said material being air-permeable and water-impermeable, includes non-woven fabric, porous plastic film, and laminate sheets thereof.

The elastic member 11 may be made of material conventionally used for such member, for example, natural or synthetic rubber, plastics such as polyurethane or plastics tending to exhibit or recover elasticity upon heat treatment. However, the present invention is not limited to use of such particular material. It should be understood that, when the relatively wide elastic member is used as in the cases of FIGS. 2 through 6, FIGS. 9, 10 and 11 (reference numeral 11b), polyurethane foam sheet is preferably used.

Although the flaps 7 each having the support portion 8 and the inner and outer branched portions 9, 10 has been described as being disposed in the crotch area of diaper, the flaps 7 may be incorporated also into the rear waist flap 4 and the flaps 5 in the crotch area or only into the flaps 4.

Provision of the flaps 7 in the crotch area of diaper as the leakage preventing means for around respective thighs of the wearer in the manner as has been mentioned above assures that, when the diaper is put on, the inner and outer branched portions 9, 10 are elastically pressed against the respective thighs without remaining in the area defined between the thighs and the pockets 14 defined at least by the respective inner surfaces of the support portions 8 and the associated inner branched portions 9 reliably block any flowing excretions. When the waist flap 4 of diaper is provided with the flap 7 as the leakage preventing means for around the waist, it is assured that the inner and outer branched portions 9, 10 are elastically pressed against the waist and the pocket 14 defined at least by the respective inner surfaces of the support portion 8 and the inner branched portion 9 reliably block any flowing excretions. It should be noted here that the function and effect provided by such leakage preventing means will be optimal when such means are disposed at opposite sides of the diaper in the crotch area.

As will be apparent from the foregoing description, the disposable diaper constructed according to the present invention is suitable as the diaper requiring no diaper cover. The leakage preventing means incorporated into this diaper are useful not only to seal around the respective thighs with elastic gathers but also to seal around the waist also with elastic gathers.

What is claimed is:

1. A disposable diaper having a front, a back and lateral sides and further including a liquid-permeable topsheet (1), a liquid-impermeable backsheet (2), an absorbent core (3) sandwiched between said sheets, and excrement leakage preventing flexible flaps (7) located outwardly with respect to said absorbent core (3), each flexible flap (7) comprising:
   (a) a support portion (8) extending upwardly with respect to a surface of the diaper,
   (b) an inner branched portion (9), an entire length of which extends inwardly from an upper part of said support portion generally parallel to the backsheet (2),
   (c) an outer branched portion (10), an entire length of which extends outwardly from the upper part of said support portion generally parallel to the backsheet (2), wherein at least one of the inner and outer branched portions is directly attached at opposite ends thereof to a body of the diaper,
   (d) at least one elastic member (11) incorporated into both said inner branched portion (9) and said outer branched portion (10) so as to form plastic gathers in these two portions,
   (e) a pocket formed by an inner surface of the support portion (8) and the inner branched portion which serves to impede the leakage of excretions from the diaper; wherein at least one of the inner and outer branched portions has a width greater than a thickness thereof.

2. A disposable diaper having a front, a back and lateral sides and further including a liquid-permeable topsheet (1), a liquid-impermeable backsheet (2), an absorbent core (3) sandwiched between said sheets, and excrement leakage preventing flexible flaps (7) located outwardly with respect to said absorbent core (3), each flexible flap (7) comprising:
   (a) a support portion (8) extending upwardly with respect to a surface of the diaper,
   (b) an inner branched portion (9), an entire length of which extends inwardly from an upper part of said support portion generally parallel to the backsheet (2),
   (c) an outer branched portion (10), an entire length of which extends outwardly from the upper part of said support portion generally parallel to the backsheet (2), wherein at least one of the inner and outer branched portions is directly attached at opposite ends thereof to a body of the diaper,
   (d) at least one elastic member (11) incorporated into both said inner branched portion (9) and said outer branched portion (10) so as to form elastic gathers in these two portions,
   (e) a pocket formed by an inner surface of the support portion (8) and the inner branched portion which serves to impede the leakage of excretions from the diaper; wherein said support portion, said inner branched portion and said outer branched portion are together formed from a single strip of material that is doubled onto itself to form said portions.

3. A disposable diaper according to claim 2, wherein said at least one elastic member extends a full width of both the inner and outer branched portions.

4. A disposable diaper having a front, a back and lateral sides and further including a liquid-permeable topsheet (1), a liquid-impermeable backsheet (2), an absorbent core (3) sandwiched between said sheets, and experiment leakage preventing flexible flaps (7) located outwardly with respect to said absorbent core (3), each flexible flap (7) comprising:
   (a) a support portion (8) extending upwardly with respect to a surface of the diaper,
   (b) an inner branched portion (9), an entire length of which extends inwardly from an upper part of said support portion generally parallel to the backsheet (2),
   (c) an outer branched portion (10), an entire length of which extends outwardly from the upper part of said support portion generally parallel to the backsheet (2), wherein at least one of the inner and outer branched portions is directly attached at opposite ends thereof to a body of the diaper,
   (d) at least one elastic member (11) incorporated into both said inner branched portion (9) and said outer branched portion (10) so as to form elastic gathers in these two portions,
   (e) a pocket formed by an inner surface of the support portion (8) and the inner branched portion which serves to impede the leakage of excretions from the diaper; wherein a width of at least one of said inner and outer branched portions is approximately equal to a height of said support portion.

5. A disposable diaper having a front, a back and lateral sides and further including a liquid-permeable topsheet (1), a liquid-impermeable backsheet (2), an absorbent core (3) sandwiched between said sheets, and excrement leakage preventing flexible flaps (7) located outwardly with respect to said absorbent core (3), each said flexible flap (7) comprising:
   (a) a support portion (8) extending upwardly with respect to a surface of the diaper, (b) an inner branched portion (9), a width of which extends about one half a distance between the support portion and an outermost longitudinal edge of the core and inwardly from an upper part of said support portion generally parallel to the backsheet (2), (c) an outer branched portion (10) extending outwardly from the support portion generally parallel to the backsheet (2), wherein both the inner and outer branched portions are directly attached at opposite ends thereof to a body of the diaper, (d) at least one elastic member (11) incorporated into both said inner branched portion (9) and said outer branched portion (10) so as to form elastic gathers in these two portions, (e) a pocket formed by an inner surface of the support portion (8) and the inner branched portion which serves to impede the leakage of excretions from the diaper.

6. A disposable diaper according to claim 5, wherein said support portion, said inner branched portion and said outer branched portion are together formed from a single strip of material that is doubled onto itself to form said portions.

7. A disposable diaper according to claim 5, wherein said at least one elastic member extends a full width of both the inner and outer branched portions.

8. A disposable diaper according to claim 5, wherein a width of at least one of said inner and outer branched portions is approximately equal to a height of said support portion.

9. A diaper according to claim 5, wherein the inner branched portion includes a width greater than a thickness.

10. A diaper according to claim 5, wherein the outer branched portion includes a width greater than a thickness.

11. A disposable diaper having a front, a back and lateral sides and further including a liquid-permeable topsheet (1), a liquid-impermeable backsheet (2), an absorbent core (3) sandwiched between said sheets, and excrement leakage preventing flexible flaps (7) located outwardly with respect to said absorbent core (3) and extending from a front longitudinal end to a rear longitudinal end of a body of the diaper, each flexible flap (7) comprising:

(a) a support portion (8) extending upwardly with respect to a surface of the diaper, (b) an inner branched portion (9), an entire length of which extends inwardly from an upper part of said support portion generally parallel to the backsheet (2), (c) an outer branched portion (10), an entire length of which extends outwardly from the upper part of said support portion generally parallel to the backsheet (2), wherein at least one of the inner and outer branched portions is directly attached at opposite longitudinal ends thereof to the front and rear longitudinal ends of the body of the diaper, (d) at least one elastic member (11) incorporated into both said inner branched portion (9) and said outer branched portion (10) so as to form elastic gathers in these two portions, (e) a pocket formed by an inner surface of the support portion (8) and the inner branched portion which serves to impede the leakage of excretions from the diaper; wherein said flexible flap is formed with a T-shape in cross-section as defined by the support portion and the inner and outer branched portions.

12. A disposable diaper having a front, a back and lateral sides and further including a liquid-permeable topsheet (1), a liquid-impermeable backsheet (2), an absorbent core (3) sandwiched between said sheets, and excrement leakage preventing flexible flaps (7) located outwardly with respect to said absorbent core (3), each flexible flap (7) comprising:

(a) a support portion (8) extending upwardly with respect to a surface of the diaper, (b) an inner branched portion (9), an entire length of which extends inwardly from an upper part of said support portion generally parallel to the backsheet (2), (c) an outer branched portion (10), an entire length of which extends outwardly from the upper part of said support portion generally parallel to the backsheet (2), wherein at least one of the inner and outer branched portions is directly attached at opposite ends thereof to a body of the diaper, (d) at least one elastic member (11) incorporated into both said inner branched portion (9) and said outer branched portion (10) so as to form elastic gathers in these two portions, (e) a pocket formed by an inner surface of the support portion (8) and the inner branched portion which serves to impede the leakage of excretions from the diaper; wherein the inner branched portion has a width, measured in a transverse direction of the diaper, which is at least three times as large as a thickness of the support portion.

13. A disposable diaper having a front, a back and lateral sides and further including a liquid-permeable topsheet (1), a liquid-impermeable backsheet (2), an absorbent core (3) sandwiched between said sheets, and excrement leakage preventing flexible flaps (7) located outwardly with respect to said absorbent core (3), each flexible flap (7) comprising:

(a) a support portion (8) extending upwardly with respect to a surface of the diaper, (b) an inner branched portion (9), an entire length of which extends inwardly from an upper part of said support portion generally parallel to the backsheet (2), (c) an outer branched portion (10), an entire length of which extends outwardly from the upper part of said support portion generally parallel to the backsheet (2), wherein at least one of the inner and outer branched portions is directly attached at opposite ends thereof to a body of the diaper, (d) at least one elastic member (11) incorporated into both said inner branched portion (9) and said outer branched portion (10) so as to form elastic gathers in these two portions, (e) a pocket formed by an inner surface of the support portion (8) and the inner branched portion which serves to impede the leakage of excretions from the diaper; wherein the inner branched portion has a width, measured in a transverse direction of the diaper, which is at least three times as large as a thickness of the support portion; and the outer branched portion has a width, measured in the transverse direction of the diaper, which is at least three times as large as the thickness of the support portion.

* * * * *